United States Patent [19]

Imburgia et al.

[11] Patent Number: 5,178,149
[45] Date of Patent: Jan. 12, 1993

[54] TRANSESOPHAGEAL PROBE HAVING SIMULTANEOUS PACING AND ECHOCARDIOGRAPHIC CAPABILITY, AND METHOD OF DIAGNOSING HEART DISEASE USING SAME

[76] Inventors: Michael Imburgia, 1602 Grey Owl Ct., Louisville, Ky. 40223; George E. Pool, 3812 Hycliffe Ave., Louisville, Ky. 40207

[21] Appl. No.: 432,543

[22] Filed: Nov. 6, 1989

[51] Int. Cl.$^5$ .................. A61B 8/12; A61N 29/00
[52] U.S. Cl. .................. 128/662.06; 128/419 P
[58] Field of Search ............ 128/419 P, 419 PG, 671, 128/642, 660.10, 662.06, 4

[56] References Cited

U.S. PATENT DOCUMENTS

| | | | |
|---|---|---|---|
| 3,951,136 | 4/1976 | Wall | 128/404 X |
| 4,198,963 | 4/1980 | Barkalow et al. | 128/419 D X |
| 4,304,240 | 12/1981 | Perlin | 128/671 |
| 4,409,986 | 10/1983 | Apple et al. | 128/715 |
| 4,476,872 | 10/1984 | Perlin | 128/642 |
| 4,517,984 | 5/1985 | Perlin | 128/642 |
| 4,574,807 | 3/1986 | Hewson et al. | 128/419 PG |
| 4,577,638 | 3/1986 | Graham | 128/671 |
| 4,640,298 | 2/1987 | Pless et al. | 128/784 |
| 4,683,890 | 8/1987 | Hewson | 128/419 PG |
| 4,706,681 | 11/1987 | Breyer | 128/642 |
| 4,706,688 | 11/1987 | Michael et al. | 128/785 |
| 4,735,206 | 4/1988 | Hewson | 128/419 D |
| 4,736,663 | 8/1988 | Uphold et al. | 128/671 |
| 4,817,611 | 4/1989 | Arzbaecher et al. | 128/642 |
| 4,917,115 | 4/1990 | Flammang et al. | 128/661.07 X |
| 4,977,898 | 12/1990 | Schwarzschild et al. | 128/662.06 |

FOREIGN PATENT DOCUMENTS 133400 3/1979 Fed. Rep. of Germany .

OTHER PUBLICATIONS

Baker and McLeod, "Osephageal Multipurpose Monitoring Probe", Anesthesia, 1983, vol. 38: pp. 892-897.

Primary Examiner—Francis Jaworski
Attorney, Agent, or Firm—Middleton & Reutlinger

[57] ABSTRACT

Transesophageal echocardiographic probe having simultaneous cardiac pacing and echocardiographic capability. The inventive probe is provided with transducer means to provide echocardiographic imaging of the ventricular wall motion of a patient's heart as it is stress-paced by a novel pacing electrode connectable to the periphery of the transesophageal probe. By locating the pacing electrode upon the periphery of the probe a selected distance from the echo transducer, placement of the pacing electrode to produce optimal atrial pacing can be optimized. A method setting forth a diagnostic protocol to achieve echocardiographic diagnosis is also disclosed.

29 Claims, 2 Drawing Sheets

TRANSESOPHAGEAL PROBE HAVING SIMULTANEOUS PACING AND ECHOCARDIOGRAPHIC CAPABILITY, AND METHOD OF DIAGNOSING HEART DISEASE USING SAME

FIELD OF THE INVENTION

This invention pertains to devices and methods for use in connection with transesophageal echocardiography. More particularly, the invention described discloses a single transesophageal probe having the capability to electrically induce activity of the heart of a patient (i.e., "pace" the patient's heart) and simultaneously produce an echocardiogram of the ventricular wall motion induced by the paced heart activity to permit accurate diagnosis of coronary disease. The invention is especially useful for those patients whose hearts, for one reason or another, cannot be adequately stress-tested.

BACKGROUND OF THE INVENTION

It is well known in the cardiologic field that diagnosing the presence or absence of coronary disease is enhanced by having the patient's heart undergo stress testing to induce a high enough heart rate at which coronary disease may be detected. However, for various reasons, approximately thirty percent (30.0%) of the patient population is unable to tolerate stress testing to produce a heart rate at which acceptable diagnosis of heart disease is possible.

It is known that a most revealing way to determine the presence and extent of coronary-disease (particularly coronary artery disease) is to monitor the ventricular wall motion of the heart operating at higher beat levels. Techniques to produce a sonogram or echocardiogram of ventricular wall motion are known, and usually involve the use of a transthoracic transducer placed on the outside of the patient's chest in vicinity to the heart to visualize heart wall motion.

At present, in addition to the unpopular (and relatively unsafe) technique of a temporary pacing by means of an intravenous pacing wire implanted in contact with the heart (i.e., the i-v pacemaker), the art has developed two general types of diagnostic tests for patients who cannot be adequately stress tested to permit accurate assessment of coronary disease. First, there is the "pill electrode" type of device, as illustrated in U.S. Pat. No. 4,817,611, whereby the patient is induced to swallow a device which may be used to artificially stimulate (i.e., pace) the heart to higher activity. A second technique is to stress the heart pharmacologically, usually by Dipryridamole. In both situations, the stressed heart's activity is then monitored by radionuclide imaging enhaced by thallium doping. The pharmacological technique has the drawback of possible irreversible medicinal side effects. The "pill electrode" is very uncomfortable to the patient, and the echocardiographic imaging modality associated with the pill electrode (i.e., transthoracic echocardiography) is often unsatisfactory.

The present invention solves the inadequacies of the prior art by providing a single transesophageal probe having the capability to both pace the patient's heart and simultaneously produce a higher quality echocardiographic image of the ventricular wall motion of the patient's heart to permit accurate diagnostic assessment of coronary disease revealed by the stress induced on the paced heart.

Physiologically, transesophageal probes are capable of being located much closer to the heart compared to other devices, since the esophagus actually lays against the heart in the vicinity of the left atrium. Because the transducer which is receiving the sonic energy produced by the reflection of the transducer's sonic output (which is reflective of ventricular wall motion of the stressed heart) is in close proximity to the heart, much closer than is possible with transthoracic echocardiography, a much improved echocardiographic image is produced. Similarly, also because of the proximity of the esophagus to the heart, the pacing electrode mounted on the transesophageal probe may be more easily and precisely placed in relation to the atrial chambers of the patient's heart to permit a more controlled, safer electrical pulse to pace the heart to desired stress levels, than is possible with the pill electrode or other techniques including pharmacological techniques to pace the heart.

SUMMARY OF THE INVENTION

The present invention disclosed and described hereinafter presents a transesophageal probe capable of simultaneous cardiac pacing and echocardiography. This is accomplished by presenting a unique transesophageal probe having an echo producing transducer presented at its distal end coupled with a novel circumferential pacing electrode located a selected distance up the distal end of the probe. By selecting the appropriate spacing, approximately 10 centimeters, between the echo transducer and the pacing electrode, this permits the probe to be placed at the optimal location to both produce paced activity and generate good echocardiological images of ventricular wall motion of the patient's heart as it is stress-paced.

It is an object of the present invention to provide a transesophageal probe capable of pacing a patient's heart to desired stress levels while simultaneously producing an echocardiogram of the ventricular wall motion of the heart in stressed activity.

It is a further object to provide a noninvasive non-pharmacological protocol to diagnose coronary disease, particularly ischemic or coronary artery disease, by simultaneously pacing and echocardiographically recording the ventricular wall motion of the patient's heart.

It is a further object of the invention to provide a bipolar pacing transesophageal probe equipped with a distal end adapted to be circumferentially attached to the outer periphery of the transesophageal probe.

It is a further object of the invention to locate the novel pacing electrode at a critical distance from the echo producing transducer on the distal end of the probe to provide optimal pacing and echocardiographic functions of the pace-stressed heart.

Other objects of the invention, as well as numerous advantages and features of the present invention, will become readily apparent from the following description of the preferred embodiment described below, from the drawings which accompany this application, and from the claims set forth at the end of the description.

DESCRIPTION OF THE PREFERRED EMBODIMENT

Figure 1:
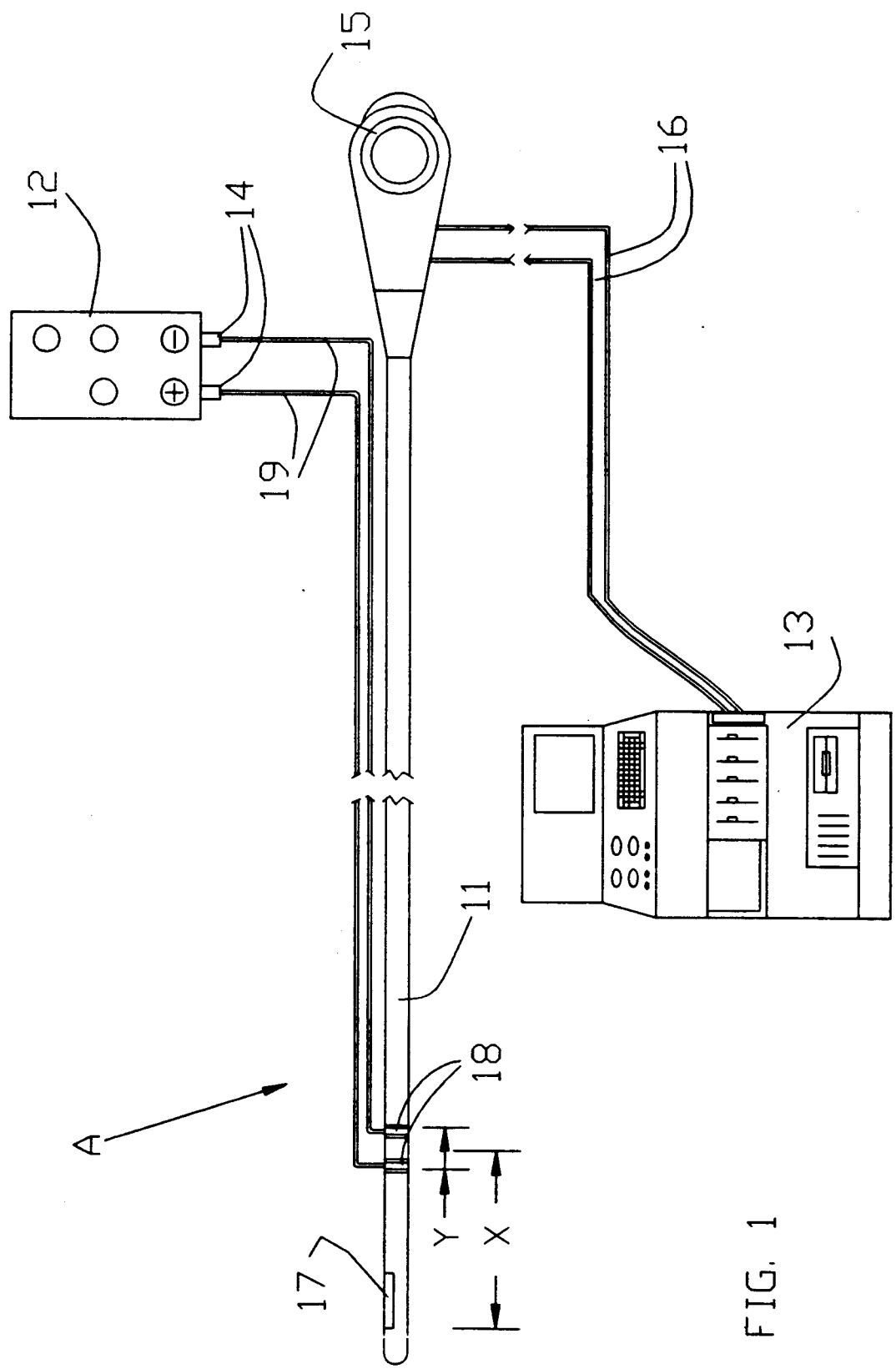
FIG. 1 is a schematic representation of the present invention showing the components thereof.

Referring to FIG. 1, there is presented a transeophageal pacing and echo probe A comprising an elongated flexible transesophageal probe 11 operatively connectable via leads 19 to the output terminals 14 of a bipolar electric cardiac pulse generator 12. Both such probes and such pulse generators are known in the art, and while many types would produce acceptable results with the present invention, we have found a Biplane Transesophageal Echocardioprobe unit manufactured by Corometrics, Inc., and a Medtronic Model 5328 pulse generator available from Medtronic, Inc. to produce acceptable results.

The transesophageal probe of the present invention is equipped with an echo-producing transducer 17 at its distal end, with the leads of the transducer 17 being fed through the interior of the probe to directional controls 15 to move the distal end of probe 11. Transducer 17. Transducer 17 is connected via cable leads 16 to an echocardiography control console and display unit 13. These units are known in the art, and we have found the Corometric Model 87 unit available from Corometrics, Inc. to provide acceptable results.

The present invention is provided with a novel pacing electrode 18 circumferentially attachable to the outer periphery of the transesophageal probe 11 and connectable via leads 19 to the output termini 14 of the cardiac pacing unit 12. The pacing electrode 18 is located a selected distance x toward the proximal end of the probe from the transducer 17 to provide optimal pacing and echocardiographic results. We have found a distance x of between 5 and 15 centimeters to produce acceptable results, with best results achieved when x is about 10 centimeters. The leads of elecrode 18 are placed circumferentially about the periphery of probe 11 in parallel spaced relationship, represented by distance y. Ring electrodes 18 may be placed in partial circumferential relation (e.g., $\frac{1}{4}$, $\frac{1}{2}$, $\frac{3}{4}$ or other desired partial peripheral coverage) or full peripheral position around the periphery of probe 11. The more of the circumference of probe 11 that is covered by ring electrodes 18, the less that probe 11 must be rotated within the patient's esophagus to place electrodes in optimal pacing position to stimulate (i.e., "pace") the patient's heart. Distance y may be varied to produce desired pacing signal characteristics, such as current density, to provide an optimal pulse generated by cardiac pulse generator 12 to stress the patient's heart to desired levels. We have found a distance of y of about 10 millimeters to be satisfactory, but it may be presented within the range of about five (5) to thirty (30) millimeters.

Figure 2:
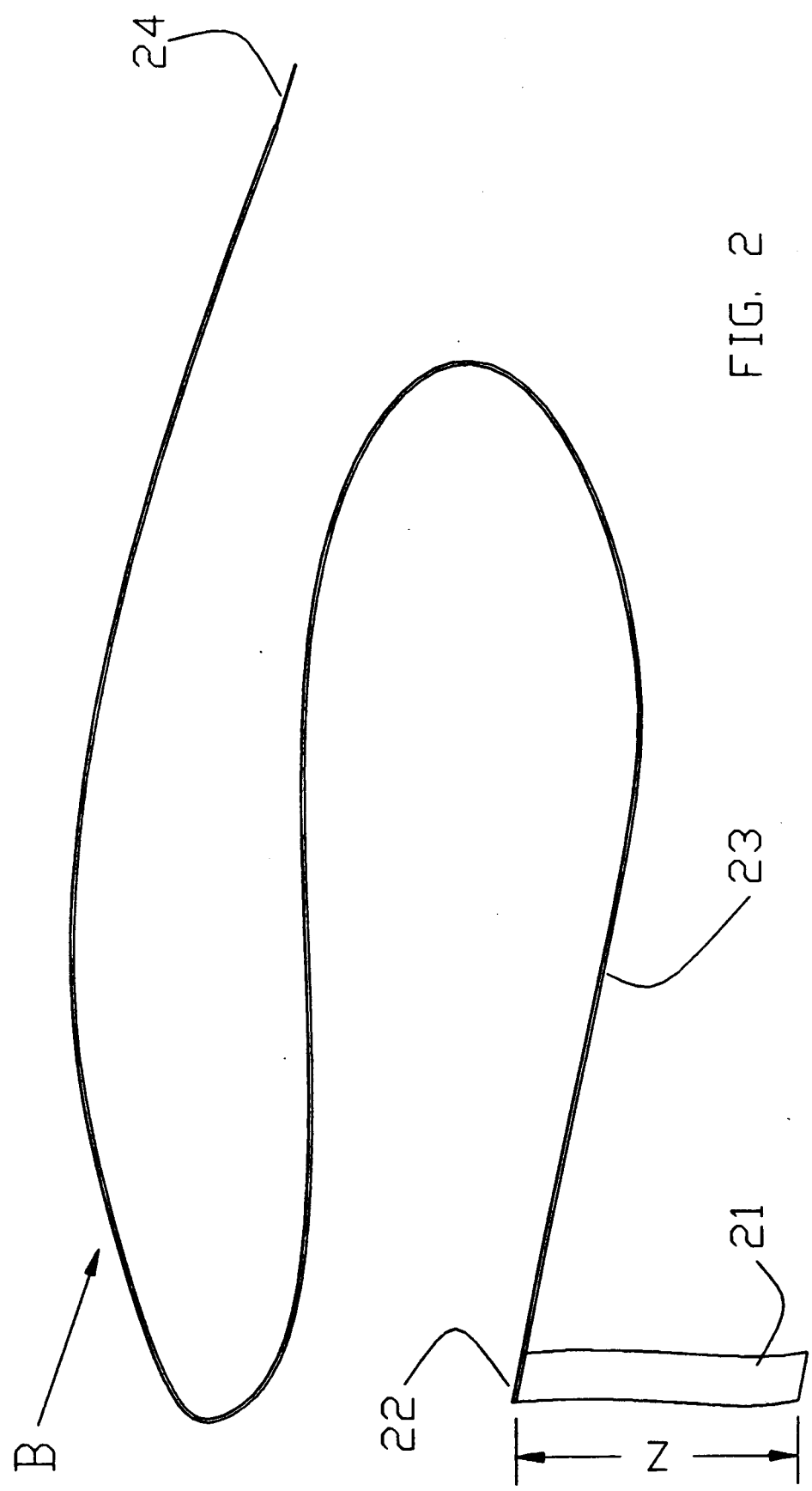
FIG. 2 is a schematic representation of the novel pacing ring electrode of the present invention, showing the components thereof.

Referring now to FIG. 2, the details of the novel pacing ring electrode B are presented. Pacing ring electrode B includes a conductive flexible lead 23 approximately one meter in length having a proximal end 24 connectable to the output termini of the electric cardiac pulse generator (shown as reference 14 in FIG. 1). The distal end 22 of lead 23 is conductively connectable to a conductive band 21 which is adaptable to be circumferentially affixed to the outer periphery of the transesophageal probe 11 at the selected location.

Band 21 may be a variety of geometries, but it has been found that a band about $\frac{3}{8}$ inch wide and 1/16 inch in thickness provides good results for pacing. The length z of band 21 is provided in sufficient length to be circumferentially affixed to a selected peripheral proportion or distance of the outer periphery of probe 11; for the type of probe used by us, a length z of about 13 millimeters works well. The surface of band 21 is smooth so as to permit both contact with the outer periphery of the probe 11 in appropriate conducting relationship and avoid trauma to the esophagus. Lead 23 may be of any flexible conductive material, and we have found that TEFLON coated insulated small gauge wire produces acceptable results. Coaxial flexible cable may also be used for lead 23.

Band 21 may be of braided copper wire or any conductively equivalent substitute and conductively connected to the distal end of lead 23 in a variety of ways. We have used tinning and soldering satisfactorily, after which we cover the conductive joint as well as the entire surface of band with copper foil tape (not shown).

To perform the simultaneous pacing and echoing upon a patient, the patient is fasted (NPO) for approximately six hours prior to the procedure. At the commencement of the procedure, the patient is placed on a heart monitor and in addition placed on a standard 12 lead electrocardiograph (ECG) or (EKG) as well as on oxymetric and blood pressure monitors. The EKG and other monitors will remain in place during the diagnostic procedure of the present invention. Just prior to the pacing/echoing procedure, the patient is given IV VERSED and sedated in normal fashion using DEMERAL or the pharmacological equivalent. Xylocaine spray may be used as a local anesthetic for the posterior pharynx. At this point the patient's at-rest heart rate is measured and recorded.

The transesophageal probe A is constructed by affixing to the outer periphery of probe 11 one or more of the novel pacing ring electrodes B constructed as set forth above. We have found that pacing ring electrode B performs best in bi-polar fashion using a pair of ring electrodes constructed according to FIG. 2, as shown at reference 18 of FIG. 1. The pair of ring electrodes is presented in parallel fashion perpendicular to the longitudinal axis of probe 11 and spaced apart about 10 millimeters and located about 10 centimeters from the transducer 17 in the distal end of probe 11. The leads 19 of pacing ring electrode B are then attached to the output terminals 14 of electric cardiac pulse generator 12. Of course, transesophageal probe A does not have to be prepared every time, and the ring electrode (unipolar) or electrodes (bi-polar) B may be permanently or semi-permanently circumferentially affixed to the outer periphery of probe 11.

When both the patient and the transesophageal endoscope A have been prepared as described above, the distal end of the probe 11 is inserted into the esophagus of the patient and advanced to a location where the atria of the patient's heart may be visualized on the echocardiography display screen of control console 13. At this point, if not previously connected, the leads 19 of ring electrode or ring electrodes B positioned at 18 on probe 11 are connected to the output terminals 14 of cardiac pulse generator 12. Probe 11 is then advanced approximately 10 centimeters more to the point where the patient's ventricles are visualized on the echocardiography screen.

At this point, the pulse generator is ready to be actuated to commence stimulating (i.e., pacing) the patient's heart to desired stress levels to permit appropriate diagnosis. Initial actuation at amperage settings of five (5) milliamperes and pulse duration of nine (9) milliseconds has been found to produce acceptable results. Beginning with a pulse strength of five milliamperes, the strength of the pulses from pulse generator 12 is increased by intervals of about two (2) milliamperes until sustained atrial capture is achieved. The patient's heart rate is then increased gradually in about twenty beat-per-minute (BPM) intervals from a base rate of the greater of 100 BPM or 20 BPM over the patient's at-rest heart rate by increasing the rate of the cardiac pulse generations from pulse generator 12. It has been found appropriate to stabilize the patient's increased heart rate at sustained capture for approximately two minutes at each BPM interval before increasing the patient's heart rate to the next BPM interval.

Good diagnostic results (i.e., good imaging of ventricular wall motion to reveal abnormalities associated with the presence or absence of ischemic or other heart disease) have been obtained when the patient's heart rate has been paced to about 150 to 160 BPM and held at that level while viewing the image of the patient's ventricular wall motion on the echocardiographic screen. When the diagnostic result has been achieved, the pulse generator is deactivated and the patient is permitted to return to his at rest heart rate, the probe is removed from the esophagus and the procedure is terminated.

Of course, it is possible that even during this noninvasive procedure the patient will undergo some distress or experience chest pain. If that occurs, or if the other monitors indicate abnormal reaction, the procedure may and should be discontinued.

The above description should be considered as exemplary only and that of the preferred embodiment only. For example, while a bipolar electric cardiac pulse generator has been hereinabove described, unipolar cardiac pulse generators are known, and those skilled in the art will appreciate that the invention herein described and claimed can function with such a unipolar pulse generator. The true spirit and scope of the present invention should be ascertained by reference to the appended claims. It is intended and desired to include within the appended claims all modifications that come within the scope of the invention.

What is claimed is:

1. A transesophageal instrument to perform simultaneous pacing and echocardiography of an organ of a patient, comprising:

an elongated probe adaptable to be inserted into the esophagus of a patient having a distal end and a proximal end;

echo producing means comprising a transducer capable of producing signals receivable and convertible into sonographic images located at a selected location near the distal end of said probe to produce a signal indicative of the sonic energy emitted by said echo producing means reflecting sonic energy off an organ of said patient and convertible into sonographic images;

organ stimulating and pacing means adaptable to the periphery of said probe and located a selected distance from said echo producing means connectable to an electrical stimulus generating device;

signal transmission means connectable to said echo producing means to transmit said signal produced by said echo producing means to a receiver to receive said signal from said echo producing means and convert said signal into a sonogram indicative of the motion of said organ of said patient; and connecting means connectable to said organ stimulating and pacing means and said stimulus generating device to transmit stimuli produced by said stimulus generating means to said organ stimulating means, whereby said probe is capable of simultaneously stimulating and pacing said organ of said patient while producing a real-time sonogram of said paced organ.

2. The invention of claim 1 wherein said organ stimulating and pacing means comprises conductive wire having a band portion at its distal end of selected length attachable to said probe a selected distance around the circumference of the periphery of said probe.

3. The invention of claim 2 wherein said selected distance comprises at least one-fourth of the circumference of said probe at the location of attachment.

4. The invention of claim 2 wherein said selected distance comprises at least one-half of the circumference of said probe at the location of attachment.

5. The invention of claim 2 wherein said selected distance comprises at least three-fourths of the circumference of said probe at the location of attachment.

6. The invention of claim 2 wherein said distal end of said organ stimulating and pacing means is attachable to said probe substantially the full circumference of said periphery of said probe at the location of attachment.

7. The invention of claim 2 wherein said band of said distal end of said organ stimulating and pacing means comprises generally flattened conductive material connectable to said conductive wire of said organ stimulating and pacing means.

8. The invention of claim 7 wherein said echo producing means comprises a transducer capable of producing signals receivable and convertible into sonographic images.

9. The invention of claim 7 wherein said organ stimulating and pacing means comprises electrical pulse generating means capable of producing electrical pulses of selected interval and strength to stimulate and pace said organ at selected activity level.

10. The invention of claim 7 wherein said organ stimulating and pacing means includes a pair of conductive leads connectable in spaced relationship to said organ stimulating and pacing means, the more proximal of said leads connectable to the positive terminal of said organ stimulating and pacing means and the second of said leads connectable to the negative terminal of said organ stimulating and pacing means.

11. The invention of claim 2 wherein said selected distance between said echo producing means and said organ stimulating means is between 5 and 15 centimeters.

12. The invention of claim 11 wherein said selected distance is about 10 centimeters.

13. A cardiologic pacing device comprising a transesophageal probe insertable into the esophagus of a patient, having a pair of ring electrodes in selected space relation to each other peripherally attachable a selected peripheral distance around the periphery of said probe and located a selected distance from the distal end of said probe to place said pair of ring electrodes in selected position in relation to the patient's heart, each of said ring electrodes including a conductive lead having a proximal end connectable to the positive or negative output terminal of an electrical cardiologic pulse generator and a distal end connectable to said ring electrodes, whereby said pacing device is capable of imparting a signal from said pulse generator to the heart of said patient.

14. The invention of claim 13 wherein said leads comprises a coaxial conductive material.

15. The invention of claim 14 wherein said connected relationship comprises circumferential relationship with a selected proportion of the outer periphery of said probe.

16. The invention of claim 13 wherein said selected peripheral relationship of said pair of ring electrodes is at least one-fourth of said outer periphery of said probe.

17. The invention of claim 13 wherein said selected peripheral relationship of said pair of ring electrodes is at least one-half of said outer periphery of said probe.

18. The invention of claim 13 wherein said selected peripheral relationship of said pair of ring electrodes is at least three-fourths of said outer periphery of said probe.

19. The invention of claim 13 wherein said selected peripheral relationship of said pair of ring electrodes is substantially all of said outer periphery of said probe.

20. The invention of claim 13 wherein said conductive material and said termini are copper.

21. The invention of claim 13 or 13 wherein said copper of said pair of leads or said coaxial cable is coated with flexible non-conductive insulating material.

22. The invention of claim 13 wherein said spaced relationship between said pair of ring electrodes comprises about 10 millimeters.

23. Method of diagnosing heart disease by simultaneously transesophageally electrically stimulating and pacing the heart of a patient and producing and recording a transesophageal sonogram of the wall motion of the patient's heart in response to the pacing signal comprising the steps of:

determining the patient's at-rest heart rate and using same as a base reference point;

inserting an elongated transesophageal probe into the esophagus of a patient, said probe having echo producing means thereon located near the distal end thereof connectable to a sonogram recording device connectable to the proximal end thereof, and having a pacing electrode comprising a pair of ring electrodes in spaced relationship a selected distance from said echo producing means attachable to the outer periphery of said probe and connectable from the proximal end of said probe to an electrical pulse generator capable of producing electrical pulses to induce ventricular activity of the patient's heart;

passing the probe lower into the esophagus until said sonogram recording device reveals a first image indicative of a selected area of the patient's heart and fixing the position of said probe within the esophagus of the patient when the sonogram recording device reveals a second sonographic image indicative of the desired area of the patient's heart;

initiating selected pulses from said electrical pulse generator to said pacing electrode whereby activity of the patient's heart is increased by stimuli from said pulse generator; and producing a continuous sonogram of motion of the selected area of the patient's heart during said stimulated heart activity, whereby coronary disease may be detected by observing abnormal heart motion in said second sonographic image produced in response to said stimulated heart activity.

24. The invention of claim 23 wherein said first sonographic image is of the atria of the patient's heart and said second sonographic image is of ventricular wall motion of the patient's heart.

25. The invention of claim 24 including the additional steps of: after said first sonographic image of the patient's atria is produced, passing said probe lower in the patient's esophagus a selected distance until the sonogram recording device produces said second sonographic image indicative of the left ventricle of the patient's heart; and rotating said probe within the patient's esophagus to place said pair of ring electrodes in optimal pacing position with respect to the patient's heart while maintaining an optimal image of said second sonographic image of said left ventricle of the patient's heart.

26. The method of claim 25 wherein said selected pulses from said cardiac pacing device begin with a pulse duration of nine (9) milliseconds and a strength of about five (5) milliamps, increased at intervals of two milliamps until sustained atrial capture is attained.

27. The method of claim 26 including the additional steps of stimulating increased activity of the patient's heart by generating increased selected pulses from said pulse generating means until the patient's heart attains the greater of 100 beats per minute or an increase of 20 beats per minute over the at-rest heart rate for the patient, then determining the presence or absence of coronary artery disease by assessing the ventricular wall motion by reference to said second image produced by said sonogram recording device.

28. The method of claim 27 including the additional steps of increasing the pulses from said pulse generating means to stimulate increase in the patient's heart rate by twenty beats per minute, holding said increased heart rate at said increased rate for two minutes, increasing the patient's heart rate by twenty beats per minute every two minutes until the first to occur of attaining selected peak heart rate or chest pain occurs, and assessing the second image produced by said sonogram recording device of the patient's ventricular wall motion at every twenty beat increase interval to determine the presence of absence of coronary artery disease.

29. The method of claim 28 including the additional step of utilizing electrocardiographic monitoring of the patient in conjunction with said simultaneous pacing and echocardiagraphy by said single transesophageal probe, whereby said method is terminated if the patient develops an abnormal electrocardiogram before said selected peak heart rate is attained.

* * * * *